United States Patent [19]

Futami

[11] Patent Number: 5,417,966
[45] Date of Patent: May 23, 1995

[54] DEPILATORY COMPOSITION

[75] Inventor: Shunichi Futami, Nagareyama, Japan

[73] Assignee: GC Corporation, Tokyo, Japan

[21] Appl. No.: 65,999

[22] Filed: May 24, 1993

[30] Foreign Application Priority Data

Jun. 1, 1992 [JP] Japan .................................. 4-163394

[51] Int. Cl.⁶ ............................................. A61K 7/155
[52] U.S. Cl. .................................. 424/73; 424/70.11;
424/78.02; 424/401; 132/202; 8/94.16; 8/160;
8/161; 523/105
[58] Field of Search ............... 424/73, 401, 70, 78.02;
132/202; 523/105; 8/94.16, 160, 161

[56] References Cited

U.S. PATENT DOCUMENTS

| | | | |
|---|---|---|---|
| 4,282,877 | 8/1981 | Mathews | 128/355 |
| 5,026,542 | 6/1991 | Baines | 424/73 |
| 5,154,919 | 10/1992 | Des Garets | 424/73 |

*Primary Examiner*—Thurman K. Page
*Assistant Examiner*—Amy Hulina
*Attorney, Agent, or Firm*—Oblon, Spivak, McClelland, Maier, & Neustadt

[57] ABSTRACT

Paste A comprising a polysulfide polymer having a specific average molecular weight and specific amounts of liquid and filler components is mixed with Paste B comprising specific amounts of an oxide or peroxide of metal, a vulcanization accelerator, a filler and a liquid component for setting at room temperature at which a depilatory composition is used. This composition causes no pain to those who use it, and is easy to use as well.

11 Claims, No Drawings

DEPILATORY COMPOSITION

BACKGROUND OF THE INVENTION

The present invention relates to a depilatory composition for removing unwanted hair from the aesthetic viewpoint. More particularly, the invention is directed to a depilatory composition that is topically applied to the site, from which unwanted hair is to be depilated, and is removed in bulk from the root of hair for complete depilation without giving any pull thereto and with little or no pain to those who use it.

So far, various depilatory methods and materials have been provided with a particular view to meeting a woman's strong desire to remove unwanted hair from the aesthetic standpoint. However, never until now has been found any means for achieving a complete and easy depilation. One a currently available approach for achieving this involves using an adhesive tape. This tape is applied to the site from which unwanted hair is to be removed, and then peeled off from that site for depilation. However, this approach, because of pulling hair, causes a sharp pain to those who rely on it, and is found to fail to attain a complete depilation as well.

There is another depilatory method in which a wax melt is applied to the site from which unwanted hair is to be removed. This method, because of making use of the adhesion, again cause is a sharp pain to those who use it, and is found to fail to achieve a complete depilation. In addition, the method is troublesome to handle, because the wax must be heated for melting.

Besides, mechanical depilatory means or depilatory jelly is used. However, these pose an acute pain problem.

Depilatory cream is used to decompose, soften and melt hair chemically. However, this cannot achieve a complete depilation, and is found to stimulate the skin as well.

As mentioned above, an easy-to-handle, safe, effective depilatory is still in strong demand.

SUMMARY OF THE INVENTION

According to the invention, the object mentioned above is achieved by the provision of a depilatory composition which consists of Paste A comprising 55 to 85% by weight of a liquid polysulfide polymer having an average molecular weight of 1,000 to 7,500, 1 to 10% by weight of a liquid component, and 10 to 40% by weight of a filler and Paste B comprising 30 to 60% by weight of an oxide or peroxide of metal, 2 to 10% by weight of a vulcanization accelerator, 2 to 30% by weight of a filler and 20 to 50% by weight of a liquid component, said Pastes A and B being mixed together at room temperature for setting.

DETAILED DESCRIPTION OF THE INVENTION

The present invention is achieved by finding that the polysulfide rubber is so rich in the affinity with the keratin of hair that it can wrap up hair. In this state, the polysulfide is set, whereby the hair can be removed completely from the root of hair with no or little pain to those who use it.

The polysulfide rubber polymer used in the invention is analogous in chemical structure to hair, and has the following general formula:

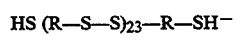

where R is $C_2H_4-O-CH_2-O-C_2H_4$.

Upon the vulcanizer added to the polysulfide polymer, the polymer chain is extended by the oxidation of the terminal mercapto group (SH) and a side chain form of mercapto group is oxidized for crosslinking, so that it can be set into rubber, as can be seen from the following reaction scheme:

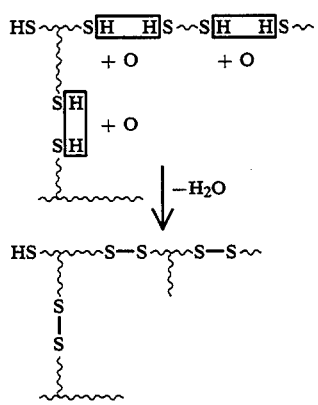

When the composition of the invention is applied to the site from which unwanted hair is to be removed, the polysulfide polymer penetrates into the hair, wherein it bonds to keratin and is set in a rubbery state. This enables the unwanted hair to be removed from the root of hair.

A polysulfide rubber polymer having a molecular weight less than 1,000 is difficult to apply, because of its high fluidity, and a polysulfide rubber polymer having a molecular weight higher than 7,500 makes the Paste A very hard so that difficulty is involved in handling it. Thus, the polysulfide polymer used in the invention must have an average molecular weight of 1,000 to 7,500 and an average viscosity, measured at 27° C., of 10 to 1,100 P.

Paste A, when containing less than 55% by weight of the polysulfide polymer, becomes insufficient in terms of rubber strength and, when containing higher than 85% of the polysulfide polymer, decreases in hardness. Thus, Paste A must contain 55 to 85% by weight of the polysulfide polymer.

The setting agent contained in the Paste B is an oxide or peroxide of metal, and should preferably be zinc oxide or peroxide, lead peroxide, magnesium peroxide, calcium peroxide, manganese dioxide, and antimony trioxide that enable Pastes A and B to provide an appropriately curable product of sufficient rubber strength that is easy to handle.

The oxides or peroxides of metals used as the setting agent may be used alone or in combination of two or more. However, Paste B, when having a setting agent content of 30% or less by weight, fails to provide a completely set rubber product. Even when used at a rate of 60% or more by weight, On the other hand, the setting agent can produce no additional improvement on its own setting effect. Thus, the amount of the oxide or peroxide of metals used as the setting agent is limited to the range of 30 to 60% by weight.

In view of the setting properties at room temperature, the vulcanization accelerator used in the invention is limited to a thiuram compound such as tetramethylthiuram monosulfide or disulfide, tetraethylthiuram disulfide, tetrabutylthiuram disulfide, or dipentamethylenethiuram tetrasulfide, a thiazole compound such as 2-mercaptobenzothiazole or 2-benzothiazyl disulfide, and a dithiocarbamate compound such as zinc dimethyl dithiocarbamate, zinc diethyl dithiocarbamate, zinc dibutyl dithiocarbamate or zinc ethyl phenyl dithiocarbamate, which may be used alone or in any desired combination of two or more. It is noted, however, that the vulcanization accelerator, when incorporated in Paste B at a rate of 2% or less by weight, makes it unable to achieve proper setting at room temperature and, when at a rate of 10% or more by weight, fails to assure a sufficient time of operation and gives rise to reversion. Thus, the rate of the vulcanization accelerator incorporated in Paste B is limited to the range of 2 to 10% by weight.

The filler is an inert inorganic component, and is suitably selected from silica, titanium oxide, alumina, calcium carbonate, calcium sulfate, and barium sulfate, which may be used alone or in any desired combination of two or more. In order to obtain Paste, however, the filler(s) should be incorporated in Paste A at a rate of 10 to 40% by weight and in Paste B at a rate of 2 to 30% by weight.

For the liquid component that is in an inert liquid state at room temperature, use must be made of a phthalate ester such as dimethyl phthalate, diethyl phthalate, isobutyl phthalate, dibutyl phthalate or dioctyl phthalate, a fatty acid ester such as dioctyl adipate, dioctyl azelate, dibutyl sebacate, dioctyl sebacate, butyl oleate or butyl stearate, and an oily component such as vegetable oil, chlorinated paraffin or liquid paraffin, which may be used alone or in any desired combination of two or more. The liquid component reduces the viscosity of Paste A for easy kneading, and makes it easy to obtain Paste B. Thus, the liquid component must be used with Paste A at a rate of 1 to 10% by weight and with Paste B at a rate of 20 to 50% by weight.

It is preferred that, when sulfur is added as a reaction assisting agent, to the depilatory composition of the present invention, vulcanizing reaction of polysulfide polymer takes place and resultant set products are made homogeneous. Sulfur used as a reaction assisting agent may be added either to the Pastes A or B.

It is possible for the depilatory composition of the present invention to be added by known and conventionally used colouring materials, perfumes etc.

The following examples are intended to illustrate and not to limit the invention.

EXAMPLE 1

| Paste A | % by weight |
| --- | --- |
| THIOCOL LP-2 (Polysulfide polymer with a molecular weight of 4,000 made by THIOCOL Co., Ltd.) | 70 |
| Finely divided silica | 10 |
| Finely divided alumina | 15 |
| Dibutyl phthalate | 3 |
| Dioctyl azelate | 2 |
| Sulfur powders | 0.5 |

The above amounts of these components were kneaded together in a kneader for 30 minutes to prepare Paste A.

| Paste B | % by weight |
| --- | --- |
| Zinc peroxide | 12 |
| Antimony trioxide | 20 |
| Tetramethylthiuram disulfide | 4 |
| Zinc ethyl phenyl dithiocarbamate | 3 |
| Finely divided silica | 16 |
| Chlorinated paraffin | 35 |
| Butyl stearate | 10 |

The above amounts of these components kneaded together in a kneader for 60 minutes to make Paste B.

The same volumes of Pastes A and B were mixed together by a plastic spatula for 60 seconds. The setting time was 10 minutes.

EXAMPLE 2

| Paste A | % by weight |
| --- | --- |
| THIOCOL LP-3 (Polysulfide polymer with a molecular weight of 1,000 made by THIOCOL Co., Ltd.) | 58 |
| Calcium carbonate | 20 |
| Calcium sulfate | 10 |
| Barium sulfate | 10 |
| Dioctyl sebacate | 2 |
| Sulfur | 0.2 |

The above amounts of these components were kneaded together in a kneader for 50 minutes to prepare Paste A.

| Paste B | % by weight |
| --- | --- |
| Lead dioxide | 45 |
| Tetrabutylthiuram disulfide | 2 |
| Titanium oxide | 28 |
| Diethyl phthalate | 3 |
| Chlorinated paraffin | 20 |
| Butyl oleate | 2 |

The above amounts of these components were kneaded together in a kneader for 80 minutes to make Paste B.

The same volumes of Pastes A and B were mixed together by a plastic spatula for 60 seconds. The then setting time was 12 minutes.

EXAMPLE 3

| Paste A | % by weight |
| --- | --- |
| THIOCOL LP-31 (Polysulfide polymer with a molecular weight of 7,500 made by THIOCOL Co., Ltd.) | 82 |
| Titanium oxide | 6 |
| Finely divided alumina | 2 |
| Dioctyl phthalate | 5 |
| Dioctyl adipate | 5 |
| Sulfur | 0.1 |

The above amounts of these components were kneaded together in a kneader for 30 minutes to prepare Paste A.

| Paste B | % by weight |
| --- | --- |
| Zinc oxide | 40 |
| Manganese dioxide | 16 |
| 2-benzothiazyl disulfide | 1 |
| Tetraethylthiuram disulfide | 4 |

-continued

| Paste B | % by weight |
| --- | --- |
| Calcium carbonate | 4 |
| Olive oil | 5 |
| Liquid paraffin | 15 |
| Dioctyl phthalate | 15 |

The above amounts of these components were kneaded together in a kneader for 60 minutes to make Paste B.

The same volumes of Pastes A and B were mixed together by a plastic spatula for 60 seconds. The setting time was minutes.

EXAMPLE 4

| Paste A | % by weight |
| --- | --- |
| THIOCOL LP-32 (Polysulfide polymer with a molecular weight of 4,000 made by THIOCOL Co., Ltd.) | 80 |
| Titanium oxide | 16 |
| Dibutyl phthalate | 4 |

The above amounts of these components were kneaded together in a kneader for 40 minutes to prepare Paste A.

| Paste B | % by weight |
| --- | --- |
| Zinc oxide | 40 |
| Calcium carbonate | 20 |
| Tetramethylthiuram disulfide | 6 |
| Chlorinated paraffin | 28 |
| Dibutyl phthalate | 6 |

The above amounts of these components were kneaded together in a kneader for 60 minutes to make Paste B.

The same volumes of Pastes A and B were mixed together by a plastic spatula for 60 seconds. The setting time was 20 minutes.

Comparative Example 1

Commercial depilatory wax was melted by heating for depilatory testing. Hot wax melt caused considerable pain to the subject, and some considerable amount of hair remained unremoved.

Comparative Example 2

Commercial adhesive depilator tape was applied to the skin of the subject, and then peeled off for depilatory testing.

When the tape was peeled off the skin, the subject had an acute pain from being pulled. Some considerable amount of hair remained unremoved.

Comparative Example 3

Commercial depilator cream was applied to the skin of the subject for depilatory testing. When the cream was wiped out as by a tampon, a part of the skin exfoliated. Almost satisfactory removal of unwanted hair was observed, but hair grew fast for the subject to recover the original state within a month.

As can be understood from the above comparative examples, conventional depilatory products are found to have grave defects; the depilatory wax is troublesome to handle due to the wax which requires heating for melt, the depilatory tape causes an acute pain to those who use it, the depilatory cream or chemical agent has an adverse influence on the skin.

As can be seen from Table 1 that follows, however, the depilatory composition of the invention causes a slight pain, if any, to those who use it, easy to handle, gives rise to no skin exfoliation or, in other words, is of great safety, and enables unwanted hair to be completely removed from the root of hair. Soft, fine hair growth is delayed, so that as long as three months are allowed by the time the next depilatory treatment.

TABLE 1

| Items | Test Materials | | | | | | |
| --- | --- | --- | --- | --- | --- | --- | --- |
| | Example 1 | Example 2 | Example 3 | Example 4 | Comparative Example 1 | Comparative Example 2 | Comparative Example 3 |
| Setting time | 10 min. | 12 min. | 15 min. | 20 min. | — | — | — |
| Influences on skin | None | None | None | None | Hot | Skin peeled | Skin partially peeled |
| Degree of pain when depilated | 2 | 2 | 2 | 2 | 3 | 5 | 1 |
| Hair removal | Good | Good | Good | Good | Considerable amount of non-depilated hair observed | Non-depilated hair observed | Depilation fair |

The setting time was measured by loading a sample in a stainless steel ring of 8.0 mm in height, 24.0 mm in inner diameter and 1.0 mm in thickness in a constant-temperature chamber maintained at a temperature 23±2° C. and a humidity of 50±10% and putting a Vicat needle (of 3.0 mm in diameter) through the sample under a load of 150 g. The setting time is then defined as being the time period from the initiation of mixing to the time at which the depth of the indentation becomes 1.0 mm or less.

The influences on the skin were estimated by what feeling the subject had when the sample was applied directly to the skin. The degree of pain was:
1. Pain hardly felt
2. Slight pain felt
3. Ordinary pain felt
4. Considerable pain felt
5. Acute pain felt Hair removal was estimated by seeing the skin.

As can be appreciated from the above, the invention is the first to develop depilatory treatment that enables soft, fine hair growth to be more delayed than achieved before, keeps the depilated site in a good condition over an extended period, and leaves the depilated site in a clear state.

What is claimed is:

1. A depilatory composition comprising Paste A, comprising: 55 to 85% by weight of a liquid polysulfide polymer having an average molecular weight of 1,000 to 7,500; 1 to 10% by weight of a viscosity reducing agent and 10 to 40% by weight of an inert inorganic filler; and, Paste B, comprising: 30 to 60% by weight of an oxide or peroxide of a metal; 2 to 10% by weight of a vulcanization accelerator; 2 to 30% by weight of an inert organic filler; and 20 to 50% by weight of a viscosity reducing agent, said Pastes A and B being mixed together at room temperature for setting; said viscosity reducing agent is one or more components selected from the group consisting of a phthalate ester selected from the group consisting of dimethyl phthalate, diethyl phthalate, isobutyl phthalate, dibutyl phthalate and dioctyl phthalate; a fatty acid ester selected from the group consisting of dioctyl adipate, dioctyl azelate, dibutyl sebacate, dioctyl sebacate, butyl oleate and butyl stearate; and an oily component selected from the group consisting of vegetable oil, chlorinated paraffin and liquid paraffin; said vulcanization accelerator being at least one component selected from the group consisting of a thiuram selected from the group consisting of tetramethylthiuram monosulfide, tetramethylthiuram disulfide, tetraethylthiuram disulfide, tetrabutylthiuram disulfide and dipentamethylenethiuram tetrasulfide; a thiazole selected from the group consisting of 2-mercaptobenzothiazole and 2-benzothiazyl disulfide; and a dithiocarbamate selected from the group consisting of zinc dimethyl dithiocarbamate, zinc diethyl dithiocarbamate, zinc dibutyl dithiocarbamate and zinc ethyl phenyl dithiocarbamate.

2. A depilatory composition according to claim 1, wherein said inert inorganic filler is one or more components selected from the group consisting of silica, titanium oxide, alumina, calcium carbonate, calcium sulfate, and barium sulfate.

3. The depilatory composition according to claim 1, wherein the oxide or peroxide of metal is one or more components selected from the group consisting of zinc oxide, zinc peroxide, lead peroxide, magnesium peroxide, calcium peroxide, manganese dioxide and antimony trioxide.

4. The depilatory composition according to claim 2, wherein said oxide or peroxide of a metal is one or more components selected from the group consisting of zinc oxide, zinc peroxide, lead peroxide, magnesium peroxide, calcium peroxide, manganese dioxide and antimony trioxide.

5. The depilatory composition according to claim 1, wherein one of Paste A and Paste B further comprises sulfur.

6. The depilatory composition according to claim 2, wherein one of Paste A and Paste B further comprises sulfur.

7. The depilatory composition according to claim 3, wherein one of Paste A and Paste B further comprises sulfur.

8. The depilatory composition according to claim 1, wherein at least one of Paste A and Paste B further comprises at least one component selected from the group consisting of coloring materials and perfumes.

9. The depilatory composition according to claim 2, wherein at least one of Paste A and Paste B further comprises at least one component selected from the group consisting of coloring materials and perfumes.

10. The depilatory composition according to claim 3, wherein at least one of Paste A and Paste B further comprises at least one component selected from the group consisting of coloring materials and perfumes.

11. The depilatory composition according to claim 5, wherein at least one of Paste A and Paste B further comprises at least one component selected from the group consisting of coloring materials and perfumes.

* * * * *